United States Patent [19]

Tokoyama et al.

[11] Patent Number: 5,157,976
[45] Date of Patent: Oct. 27, 1992

[54] POWDER GRANULE SAMPLE INSPECTION APPARATUS

[75] Inventors: Katsumi Tokoyama; Tadao Fukuda, both of Osaka, Japan

[73] Assignee: Hajime Industries Ltd., Tokyo, Japan

[21] Appl. No.: 741,218

[22] Filed: Aug. 2, 1991

Related U.S. Application Data

[63] Continuation of Ser. No. 558,746, Jul. 27, 1990, abandoned.

[51] Int. Cl.⁵ ............................................. G01N 15/02
[52] U.S. Cl. .................................................... 73/865.8
[58] Field of Search ............... 73/864.81, 865.8, 865.5, 73/866, 863.21; 358/106, 107; 209/580–582

[56] References Cited

U.S. PATENT DOCUMENTS

| | | | |
|---|---|---|---|
| 2,353,828 | 7/1944 | Hyde | 73/863.21 |
| 3,719,089 | 3/1973 | Kelsall et al. | 73/865.5 |
| 4,887,475 | 12/1989 | Austin et al. | 73/866 |
| 4,946,046 | 8/1990 | Affleck et al. | 209/580 |

FOREIGN PATENT DOCUMENTS

| | | | |
|---|---|---|---|
| 3443476 | 5/1986 | Fed. Rep. of Germany | 209/581 |
| 2632879 | 12/1989 | France | 209/582 |
| 0164331 | 12/1980 | Japan | 73/865.8 |
| 0223737 | 12/1983 | Japan | 73/863.21 |
| 0279138 | 11/1988 | Japan | 73/865.5 |
| 0584231 | 12/1977 | U.S.S.R. | 73/865.5 |
| 0696270 | 11/979 | U.S.S.R. | 73/865.8 |
| 2012948 | 8/1979 | United Kingdom | 73/865.5 |

Primary Examiner—Robert Raveis
Attorney, Agent, or Firm—Bauer & Schaffer

[57] ABSTRACT

A selected sampling of powder granules is fed penumatically from an on-line tube to a separator in which granules are separated from the air and transferred to an endless conveyor in a single layer. The selected granules are inspected for metallic foreign particles and thereafter for moisture ratio of the sampled power granules, and number and size of colored foreign particles or the like while on the conveyor.

2 Claims, 2 Drawing Sheets

POWDER GRANULE SAMPLE INSPECTION APPARATUS

This is a continuation of Ser. No. 558,746, filed Jul. 27, 1990, now abandoned.

BACKGROUND OF THE INVENTION

1. Field of the Invention

The present invention relates generally to apparatus for inspecting powder granule samples and particularly to apparatus that continuously and automatically conducts plural inspections of pharmaceutical or plastic raw materials or the like.

2. Description of the Prior Art

Conventionally, the inspection of samples of powders or granules such as pharmaceutical, plastic material, or the like, to detect the existence of metallic foreign particles mixed into the powders or granules, the number and size of colored foreign particles mixed into the powders or granules, the moisture ratio thereof, etc. were respectively conducted by manual means. Accordingly, in order to conduct plural inspections, so much manual labor and time were consumed that the characteristics of the sample could change during the course of the inspection, resulting in imprecise and inferior data.

OBJECTS AND SUMMARY OF THE INVENTION

Therefore, it is an object of the present invention to provide apparatus for inspecting powder granule samples that continuously and automatically conduct plural categories of inspection in the manner that data with high accuracy can be obtained.

According to an aspect of the present invention, the apparatus for inspecting powder granule samples comprises:

a) means for pneumatically feeding a selected sample of powder granules;

b) means for separating the granules from the air in said fed sample;

c) means for transferring the separated granules onto a continuous conveyor;

d) means for spreading the powder granules across the conveyor in a single layer; and e) means for visually inspecting the sampled powder granules in the one layer on said conveyor.

Additional and other objects, features, and advantages of the present invention will become apparent from the following description taken in conjunction with the accompanying drawings.

DESCRIPTION OF THE PREFERRED EMBODIMENTS

In the embodiment described herein, it is preferred that the inspection of the powder granule sample be conducted under a closed and clean atmosphere where outside dust or foreign particles or the like do not invade the sample.

Figure 1:
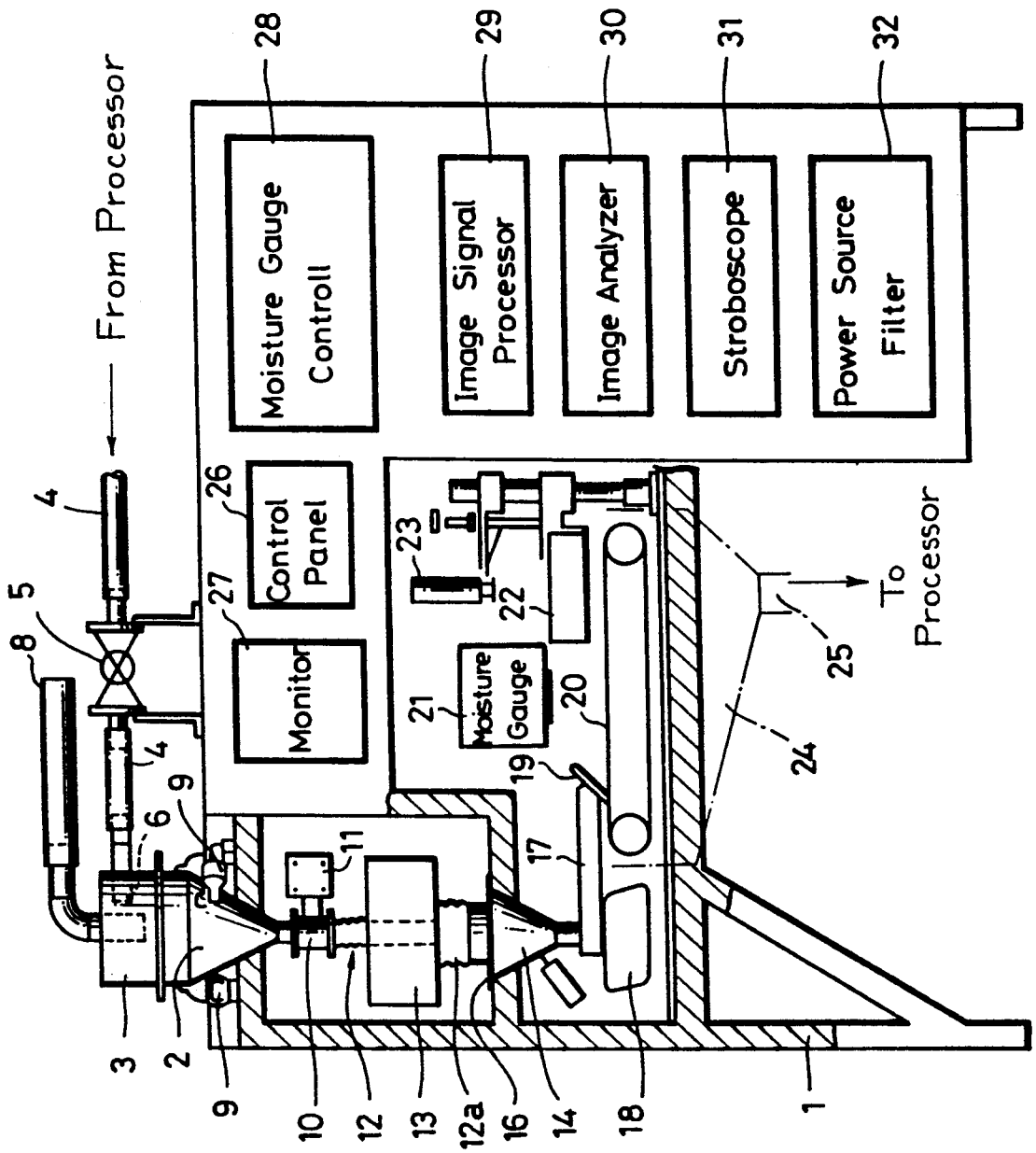
FIG. 1 is a partially sectional view of a powder granule sample inspection apparatus according to the present invention.
Figure 3:
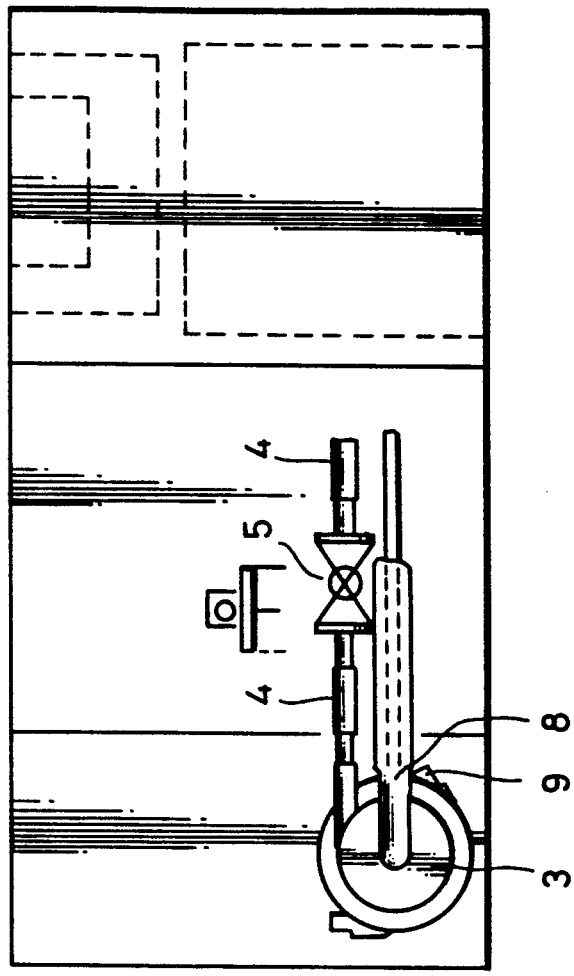
FIG. 3 a top view of the apparatus of FIG. 1.
Figure 2:
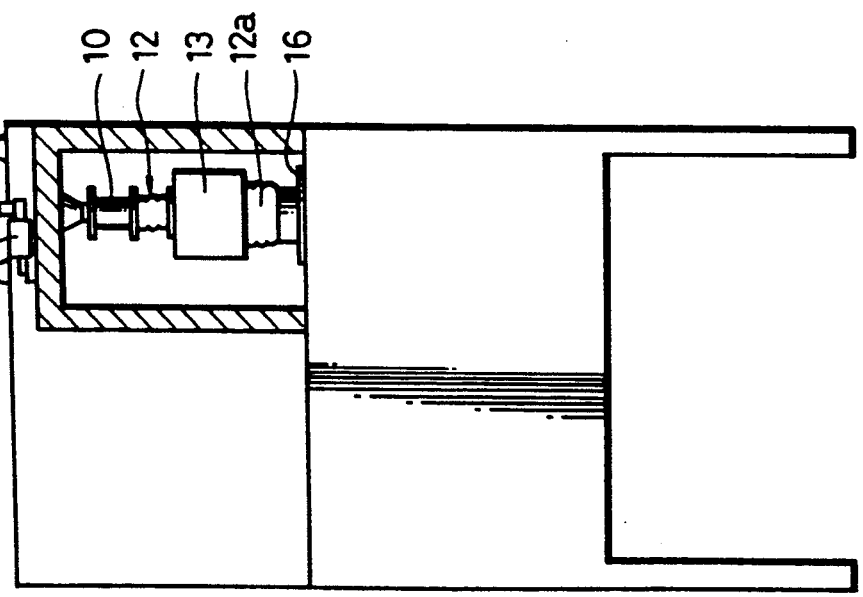
FIG. 2 is a partially sectioned front end view of the apparatus of FIG. 1.

In FIG. 1, the apparatus is housed in a main frame 1 having a first hopper 2 protruding downwards through the top of the frame 1 and resting on a load cell 9 secured to the frame 1. A cyclone 3 is installed above the upper opening of the hopper 2. One end of a sample transfer tube 4 communicates with the interior of the cyclone 3 through an ejection nozzle 6, while the other end of the transfer tube 4 communicates with a sampling nozzle (not shown in the drawings) that provides sample specimens of the powder or granule (for example, polyvinyl chloride powders or pellets) from an on-line processor (not shown in the drawings). A close and/or open valve 5 is installed midway along the transfer tube 4. Also, a pneumatic blowout pipe 8 is connected to the top of cyclone 3.

A connection tube 12 extends from the bottom outlet of the first hopper 2, straight downwards into a second hopper 14. At the upper end of the connection tube 12 is situated a ball valve 10 having a valve controller 11 which adjusts the opening of the valve 10. A metal detector 13 is installed about the tube 12 to inspect for the existence of metallic foreign particles, for example, magnetic foreign particles within the specimens dropping down inside the tube 12. Further, the lower portion 12a of the tube 12 below the outlet of the metal detector 13 is made of a bellows which sits on the cap 16 of the second hopper 14.

The outlet at the bottom of the second hopper 14 is positioned on the top of one end of a horizontal trough 17. The other end of trough 17 is positioned over the starting point of belt conveyor 20. An electromagnetic coil 18, which vibrates or shakes the trough 17, is installed below the trough 17.

A scraper 19 is located above the starting point of belt conveyor 20, functioning to evenly spread individual specimens in the conveyed sample into a single layer of uniform width across the belt. Mounted above the belt 20 are a moisture gauge 21, which measures the moisture ratio of the conveyed sample; a strobo diffusion hood 22, which intermittently irradiates the sample; and a television camera 23, which photosenses the sample to detect the number and size of the colored foreign particles contained in the sample. In this embodiment, the belt conveyor 20 comes to an end a short distance from where it passes under the television camera 23 and above a third hopper 24 having an outlet 25 for receiving the specimens.

A control panel 26 which functions to control the operation of the entire apparatus, a monitor 27 which displays the image photosensed by television camera 23, and a moisture gauge controller 28 which controls the moisture gaug 21 and at the same time indicates the moisture ratio thus detected are all housed in the frame 1. In addition, an image signal processor 29 and an image analyzer 30 which analyzes the video signals from the television camera 23, determining the number and size of the colored foreign particles, are also so provided. A stroboscope 31, which controls the cycles of the strobo diffusion hood 22; a power source filter 32, which adjusts the power source; and a computer (not shown) complete the control apparatus.

The function of this embodiment of the present invention shall now be explained.

At the occasion when the powder granule in the on-line processor is to be sampled, valve 5 is opened, and a selected number of specimens are removed from the inline system and pneumatically transferred through the transfer tube 4. The selected powder or granule specimens are blown into cyclone 3 by the blowout nozzle 6 and are separated from the carrier air in the cyclone 3 by the cyclonic action thereof. The separated powder or granule specimens accumulate in the first hopper 2 while the separated air is removed by the air blowout tube 8. The accumulated sample is weighed by the load cell 9 so that when a predetermined volume is accumulated, valve 5 closes and ball valve 10 is opened by the valve controller 11 so that a certain specific volume, as necessary for the subsequent inspection, is continuously ejected from the first hopper 2 down the connection tube 12. At this time, magnetic foreign particles contained with the powder granule are sensed by the metal detector 13. The falling powder granules accumulate inside the second hopper 14, where at this time the air inside the second hopper 14 is exhausted through the bellows portion 12a. The granules that have accumulated in the second hopper 14 are fed out at a constant volume onto the trough 17 which is vibrated by electromagnetic coil 18 and is subsequently supplied onto the belt conveyor 20, being evenly spread in a layer of uniform thickness on the surface of the conveyor 20 by the scraper 19.

The granules on the belt conveyor 20 are measured for their moisture content by the moisture gauge 21 while passing beneath the same. Then, in a sequential manner, the specimens are intermittently irradiated beneath the strobo diffusion hood 22 and photosensed by the television camera 23 so that the number and size of any colored foreign particles within the powder granules are measured. Thereafter, the conveyed granules are dropped into the third hopper 24 to be accumulated therein.

The related data, i.e. the existence of magnetic foreign material within the powder granule, the moisture ratio of the powder granule, the number and size of colored foreign particles contained in the powder granule are memorized in the computer (not shown in the drawings) and the powder granule is then fed back and to the on-line processor, via outlet 25 to be used.

A practical example of the components of powder granule inspection of the present invention is hereunder illustrated.

Power source—AC100V, 50/60 Hz, 40A
Pneumatic source—4 Kg/cm², 200 Nl/min.

When the inspected subject is polyvinyl chloride resin powder (diameter 80-150 microns), the detectors and sensors determine the existence of:
1. Colored foreign particles; and foreign particles of black, brown and yellow appearing on their surfaces larger than 100 microns;
2. Magnetic foreign particles larger than SS dia. 200 microns, SUS dia. 700 microns; and
3. Moisture content: Min. 0–0.1% Max 0–95% +0.5%

As above stated, the inspection apparatus of the present invention makes it possible to continuously and automatically conduct the inspection of the existence or not of magnetic foreign particles mixed into the powder granule sampled, the moisture content ratio of the sample, as well as the number and size of colored foreign particles within the sample of the powder granule in a container on-stream manner.

Further, since such multicategorized inspections can continuously and automatically conducted, it is possible to eliminate manpower and also obtain inspection data of high precision. Especially, due to the fact that the sample on the surface of the belt conveyor 20 is accurately spread into a uniform thickness layer by the scraper 19, the moisture content ratio of the sample, and the number and size of the colored foreign particles in the sample can be measured with high reliability. Further, the same select lot of specimens is inspected for each of the plural test categories mentioned above within a relatively short time. Consequently, any changes in the characteristics and quality of the specimens within the sample are reduced to a minimum, resulting in a more accurate and precise inspection of the selected sample.

The present invention is not limited to the need to inspect for all of the items such as the moisture content ratio of the sample and number and size of colored foreign particles within the sample while the sample is on the belt conveyor 20, but inspection may be made of less than all. Further, the inspection items need not be limited to those explained above, but the present invention may also be applied to the detection of grain size, melting point, or specific gravity, etc. as well as other factors.

The metal detector 13 can detect not only magnetic foreign material but also metallic foreign material such as nonmagnetic material, for instance.

Further, in lieu of the trough 17, a screw conveyor or the like and in lieu of the belt conveyor, a rotary table may be used.

It will be apparent that many modifications and variations could be effected by one skilled in the art without departing from the spirit or the scope of the novel concepts of the present invention so that the spirits or scope of the invention should be determined by the appended claims only.

We claim as our invention:

1. Apparatus for detecting the characteristics of a sample of granular material taken from a continuous processing system comprising means for pneumatically diverting a predetermined sample of said granular material from the processing system, means for removing the air from the granular material in said sample and dropping said granular material into a hopper, means for detecting the existance of metallic material in said granular material as it drops to said hopper, means for determining a predetermined volume of said granular material and transporting said predetermined volume onto the surface of a horizontally disposed belt conveyor, means for arranging the granular material across the surface of the belt conveyor into a contiguous layer having a uniform depth of one layer, means for measuring the moisture of said granular material as it moves along said belt conveyor, means for visually inspecting said granular material on said belt conveyor and means for returning said sampled granular material to the processing system.

2. The apparatus according to claim 1, wherein said visual inspection means comprises a television camera connected and an image signal processor analyzer.

* * * * *